US00PP17947P3

(12) United States Plant Patent
Darvas

(10) Patent No.: US PP17,947 P3
(45) Date of Patent: Aug. 28, 2007

(54) AVOCADO ROOTSTOCK NAMED 'MERENSKY 1'

(50) Latin Name: *Persea americana Mill.*
Varietal Denomination: Merensky 1

(75) Inventor: Jozsef Darvas, Letsitele (ZA)

(73) Assignee: Westfalia Technological Services, Tzanenn (ZA)

( * ) Notice: Subject to any disclaimer, the term of this patent is extended or adjusted under 35 U.S.C. 154(b) by 0 days.

(21) Appl. No.: 11/127,349

(22) Filed: May 11, 2005

(65) Prior Publication Data

US 2006/0260017 P1 Nov. 16, 2006

(51) Int. Cl.
*A01H 5/00* (2006.01)

(52) U.S. Cl. ..... Plt./200
(58) Field of Classification Search ..... Plt./200
See application file for complete search history.

(56) References Cited

U.S. PATENT DOCUMENTS

PP15,309 P3 * 11/2004 Kohne ..... Plt./200

OTHER PUBLICATIONS

UPOV–ROM GTITM, Plant Variety Database, 2006, GTI Jouve Retrieval Software, citation for avocado 'Merensky'(1 page total).*
UPOV–ROM GTITM, Plant Variety Database, 2006, GTI Jouve Retrieval Software, citation for avocado 'Merensky 1' (1 page total).*
South African Plant Variety Journal, Dec. 2003, p. 19, (2 pages total).*
Internet website "Subtropical Fruit News", vol. 7, No. 1, 1999, p. 4. (4 pages total).*

* cited by examiner

*Primary Examiner*—Anne Marie Grunberg
*Assistant Examiner*—S. B. McCormick-Ewoldt
(74) *Attorney, Agent, or Firm*—Kelly Lowry & Kelley, LLP

(57) ABSTRACT

A new and distinct variety of *Persea americana* tree having strong resistance to *Phytophthora cinnamomi* and tolerance to salinity, and used as a rootstock.

6 Drawing Sheets

DESCRIPTION

Botanical/Commercial classification: *Persea americana* Mill./Avocado Tree.

Varietal denomination: 'Merensky 1'.

SUMMARY OF THE INVENTION

This invention relates to a new and distinct variety of an avocado rootstock that is known by the varietal name 'Merensky 1'.

In the 1970's and early 1980's widespread outbreaks of *Phytophthora cinnamomi* root rot (P.c.) had devastating effects on most avocado trees grown at Westfalia Estate. The use of clonal rootstocks (such as 'Duke 7', introduced to South Africa in 1978 from California) had not yet made much impact and there were very noticeable tree health differences between individual avocado trees at Wesfalia Estate at that time. Fungicides, effective against P.c. were not available. In this period, i.e. in the late 1970's and early 1980's, a healthy seedling avocado tree was selected at Westfalia Estate where it was growing in waterlogged conditions. The parentage of this healthy seedling avocado tree is unknown. Vegetative propagation material was taken from this extraordinarily healthy avocado tree to graft several avocado rootstocks with this material. Experimental clonal propagation (asexual propagation) of this rootstock was undertaken at the Westfalia nursery. Results obtained from experimental plantings showed the 'Merensky 1' variety to be promising in terms of fruit production and resistance to *Phytophthora cinnamomi* root rot. In the 1980's budwood of the 'Merensky 1' variety was made available for academic testing. It was found that the 'Merensky 1' variety had an additional beneficial characteristic, namely its salinity tolerance as compared to available commercial avocado rootstocks. This and subsequent asexual propagation confirmed the new variety to be stable and that progeny formed is true to type. Had the variety not been discovered and carefully preserved, it could have been lost to mankind. The 'Merensky 1' variety is believed to be well-suited as a rootstock, wherein other commercial varieties are grafted thereon for avocado fruit production. The 'Merensky 1' variety can be distinguished from all previously known avocado varieties.

BRIEF DESCRIPTION OF THE PHOTOGRAPHS

The accompanying photographs show specimens of the tree and plant parts of the new 'Merensky 1' variety.

DETAILED DESCRIPTION

Figure 1:
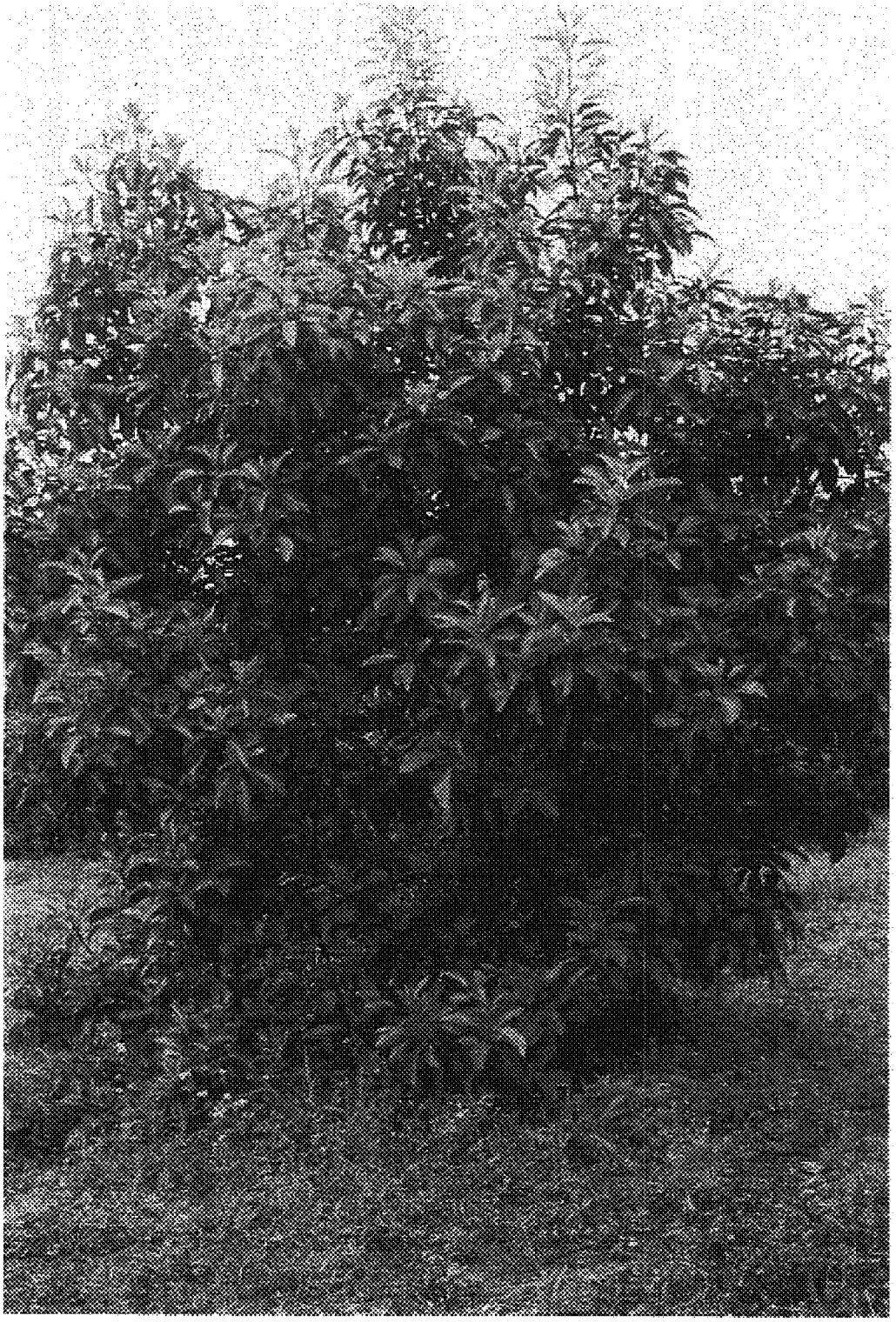
FIG. 1 illustrates a three-year old topworked tree of the 'Merensky 1' variety while growing at Westfalia Estate, South Africa.
Figure 2:
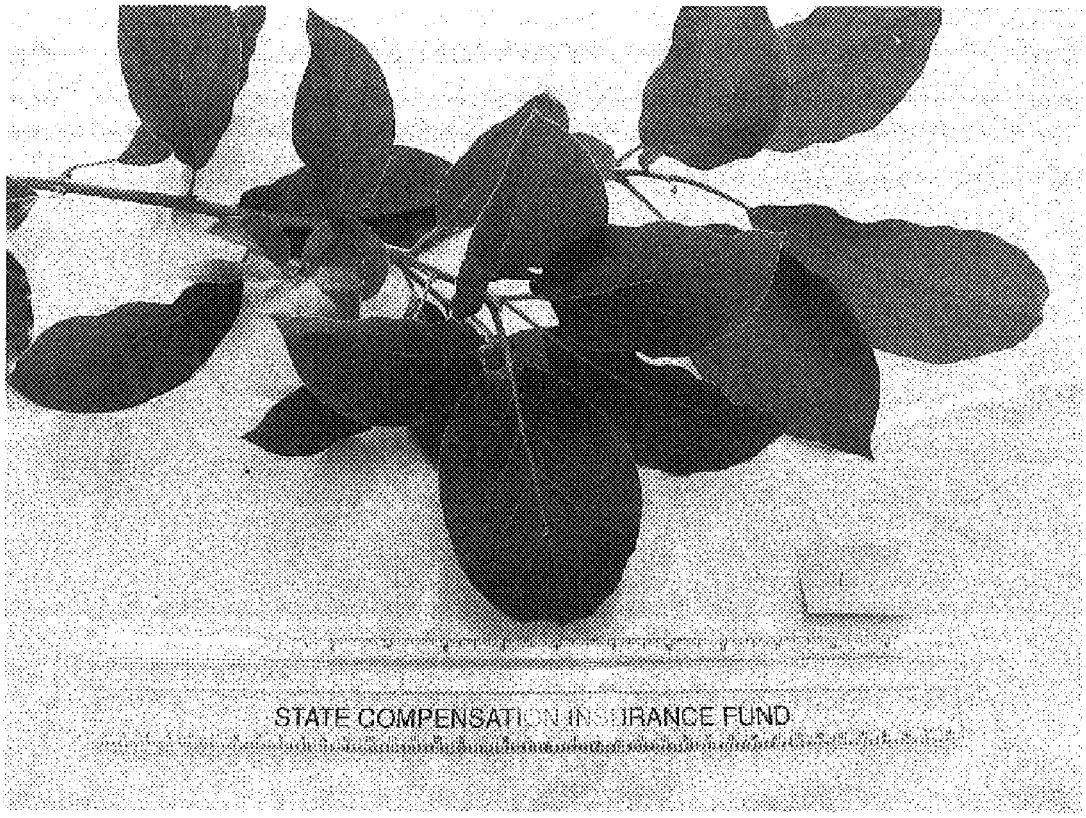
FIG. 2 illustrates typical mature foliage of the 'Merensky 1' variety, with dimensions in centimeters and inches shown below.
Figure 3:
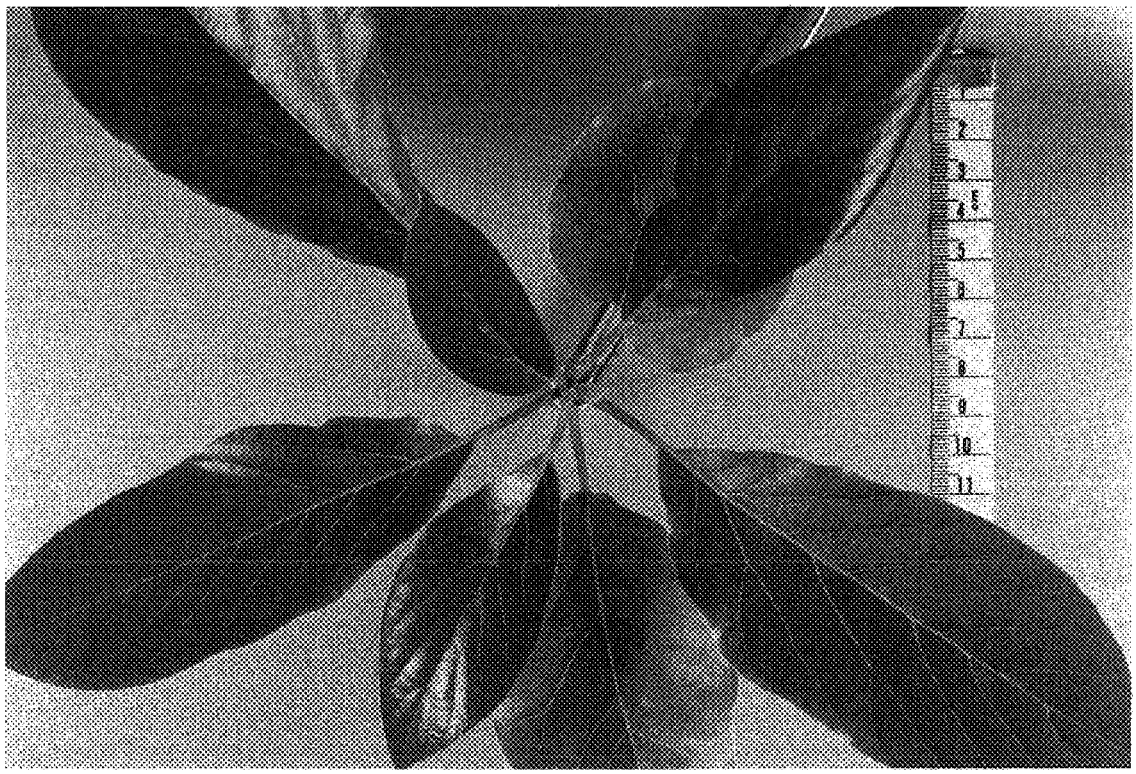
FIG. 3 illustrates typical flush foliage of the 'Merensky 1' variety with dimensions in centimeters shown on the right.
Figure 4:
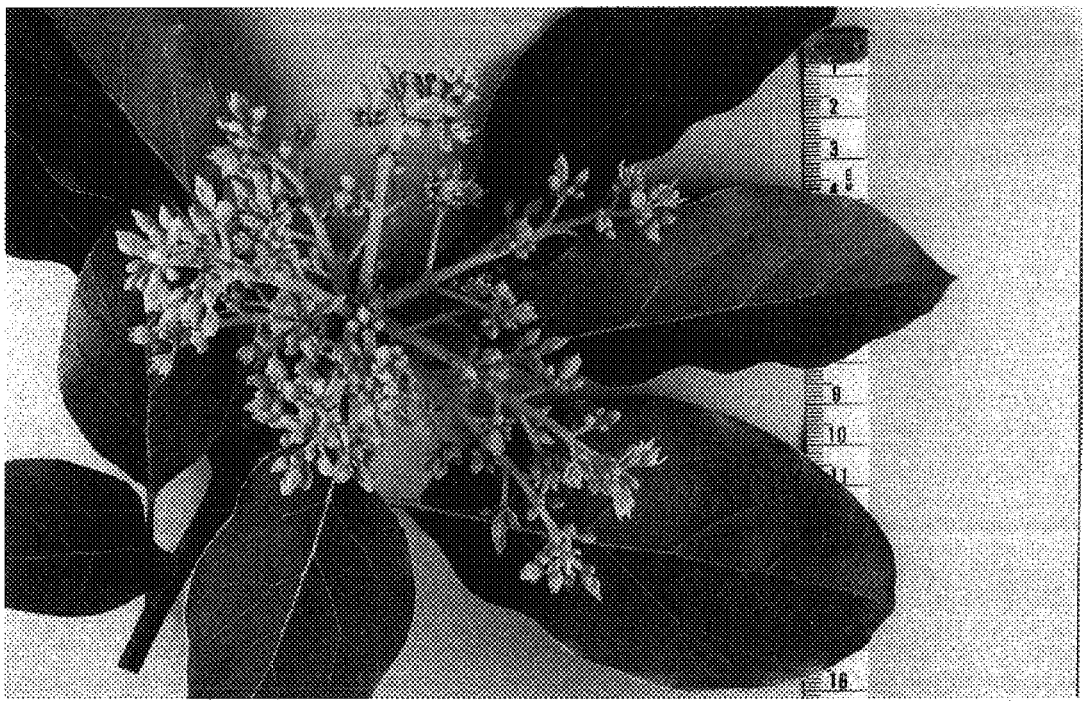
FIG. 4 illustrates typical inflorescence of the 'Merensky 1' variety with dimensions in centimeters shown on the right.
Figure 5:
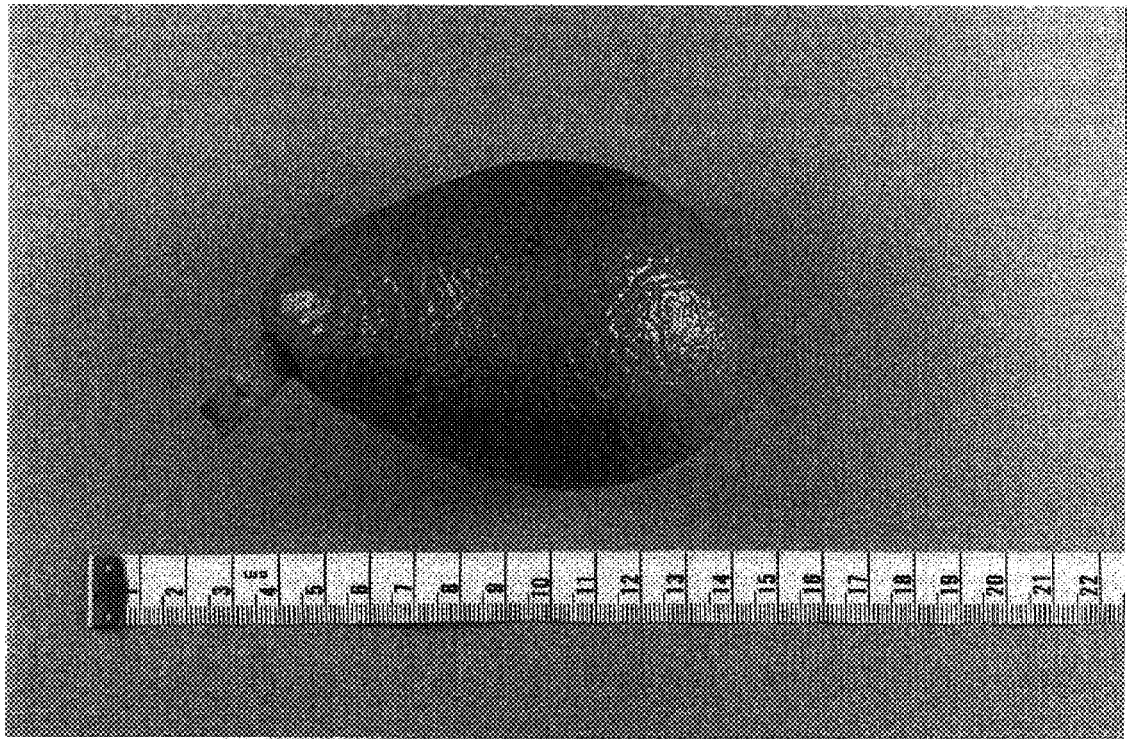
FIG. 5 illustrates a typical external view of the fruit of the 'Merensky 1' variety, with dimensions in centimeters shown below.
Figure 6:
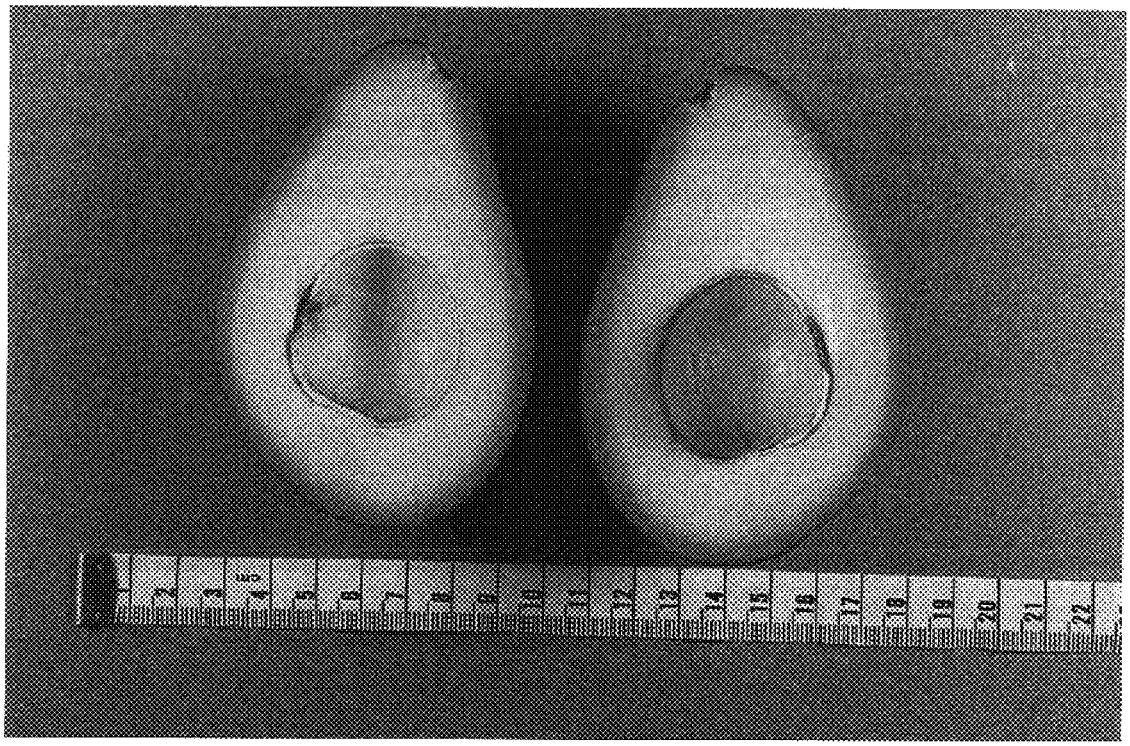
FIG. 6 illustrates typical internal views of the fruit of the 'Merensky 1' variety, with and without the seed, and dimensions in centimeters shown below.

In those instances where precise color assessment can be made, references are to The Royal Horticultural Society (R.H.S.) Colour Chart. In other instances, generally, color terms are used in accordance with an ordinary dictionary significance. The instance cultivar 'Merensky 1' is described as a plant as a whole in the following description, with the exception as a rootstock for a specific scion when reference is made to root rot resistance and salinity tolerance. The following description is taken from a three-year old topworked tree located at Westfalia Estate, Waterval section, South Africa. Reference to other varieties, and particularly the 'Merensky 2' (U.S. Plant Pat. No. 15,309 P3) is for comparative purposes of a topworked tree of approximately the same age.

Cultural conditions: Westfalia Estate, Waterval section, is situated in north-eastern South Africa (latitude 23.45 S, longitude 30.05 E, altitude 750 m above sea level). The soil type is a fine-loamy, mixed paleudult (USDA, 1975. Soil Taxonomy, Soil Conservation Service, Agriculture Handbook No. 436, Washington) with a clay content of 40%. Soil analysis prior to planting indicated a need for phosphate and pH adjustment. Superphosphate was applied to address the phosphate needs and the low soil pH (5.6) was amended to pH 6.5 by applying dolomitic lime. Nutrition requirements are based on annual leaf analyses and fertilizers spread under the tree by hand. There is a deficiency of the trace elements zinc and boron which are supplemented annually. Soil erosion is prevented by planting an annual legume cover crop. Soil moisture is monitored by means of tensiometers and irrigation is applied by micro-sprinklers aimed to wet 100% of soil in the drip zone. Climatic data: Long term average monthly maximum (MAXT)/minimum (MINT) temperatures and monthly rainfall for Westfalia Estate, Waterval section:

TABLE 1

| | JAN | FEB | MAR | APR | MAY | JUN | JUL |
|---|---|---|---|---|---|---|---|
| MAXIMUM TEMPERATURE (° C.) | 27.8 | 28.1 | 27.2 | 25.7 | 23.9 | 21.6 | 22.3 |
| MINIMUM TEMPERATURE (° C.) | 17.2 | 17.7 | 16.7 | 13.9 | 9.8 | 5.7 | 5.8 |
| RAIN (mm) | 149.3 | 245.4 | 153.8 | 107.1 | 28.5 | 30.9 | 5.0 |

| | AUG | SEP | OCT | NOV | DEC | YEAR |
|---|---|---|---|---|---|---|
| MAXIMUM TEMPERATURE (° C.) | 23.4 | 24.3 | 25.4 | 26.5 | 26.9 | 25.3 |
| MINIMUM TEMPERATURE (° C.) | 7.6 | 10.8 | 13.0 | 14.7 | 16.7 | 12.5 |
| RAIN (mm) | 21.8 | 62.9 | 107.5 | 106.5 | 161.3 | 1180 |

Tree: Growth habit — Spreading.

*Vigor.*—No data is available to quantify the vigor of the ungrafted 'Merensky 1' tree. However, data on the vigor of 'Hass' grafted onto the rootstock 'Merensky 1', as determined by trunk circumference measurement in Years 2–6 after planting in an orchard with high *Phytophthora cinnamomi* pressure at Westfalia Estate, South Africa is provided below.

TABLE 2

| | Trunk circumference (cm) | | | | |
|---|---|---|---|---|---|
| Rootstock | Year 2 | Year 3 | Year 4 | Year 5 | Year 6 |
| 'Merensky 1' | 20.4 | 25.9 | 29.8 | 32.3 | 37.3 |
| 'Merensky 2' | 18.1 | 23.6 | 27.5 | 30.2 | 34.9 |

*Size.*—Medium. The typical tree size of a three-year old topworked 'Merensky 1' is 3.8 meters in height and 4.1 meters in width. By comparison, the dimensions of a three-year old topworked 'Merensky 2' tree is 4.0 meters in height and 3.6 meters in width.

Branch:

*Color.*—The color of the one-year old branch is green (RHS 147B). Smoothness — the smoothness of the bark of a one-year old branch is smooth.

*Lenticels.*—The lenticels of a one-year old branch are inconspicuous.

Main stem:

*Color.*—Grey brown (RHS 199B and N199B).

*Texture of bark.*—Corky.

Young shoot (flush):

*Intensity of anthocyanin coloration.*—Weak. By comparison, it is medium in 'Merensky 2'.

*Color.*—Greyed-orange (RHS 176A).

*Conspicuousness of lenticels.*—Medium.

*Color of lenticels.*—Purple (RHS 187C).

*Size of lenticels.*—1.0 mm long.

*Concentration of lenticels.*—+/−30 lenticels per square cm.

*Color of upper side.*—Orange-brown (RHS 172A).

*Glossiness of upper side.*—Medium.

*Color of lower surface.*—Greyed-orange (RHS 174A).

Mature leaf:

*Length.*—18.4 cm. By comparison 17 cm for 'Merensky 2'.

*Width.*—8.6 cm. By comparison 7.0 cm for 'Merensky 2'.

*Ratio length/width.*—2.1. By comparison 2.4 for 'Merensky 2'.

*Shape.*—Lanceolate to elliptic.

*Color of upper side.*—Dark green (RHS 147A).

*Color of lower side.*—Medium green (RHS N138B). By comparison 'Merensky 2' is medium green (RHS N138C).

*Glossiness of upper side.*—Medium.

*Prominence of veins on lower side.*—Prominent and in relief.

*Color of veins.*—Yellow-green (RHS N144A).

*General shape and cross-section.*—Flat.

*Reflexing of apex.*—Absent.

*Color of petiole.*—Yellow-green (RHS 145A).

*Anise aroma.*—Absent. In contrast in 'Merensky 2', it is present.

*Margin.*—Leaf margin has weak undulation of margin.

*Leaf apex shape.*—Reflexing of apex is absent.

*Leaf base shape.*—Leaf shape is lanceolate to eliptic with the appropriate leaf base shape of the leaf.

*Length of leaf petiole.*—Approximately 7.5 cm.

*Leaf arrangement.*—Is somewhat upright in nature, as illustrated in the accompanying photographs.

Flower:

*Bud size.*—Approximately 6 mm in length and approximately 4 mm in diameter.

*Bud shape.*—Ovoid.

*Bud color.*—Commonly near yellow-green group (RHS 149D).

*Opening.*—Belongs to Group "B", female opening (i.e. with mature pistil) occurs in the afternoon, the flower closes over night, and male opening (i.e. with mature stamens) occurs the next morning; the flower's opening cycle lasts 20–24 hours. The "B" flower type is the compliment of "A" ('Hass'). Commonly avocados of the "B"-type are used for enhancing pollination of 'Hass'.

*Petals.*—Borne in two whorls of three perianth lobes. The petals possess entire margins and petal coloration is near yellow-green (RHS 145D).

*Stamen.*—There commonly are nine fertile stamens with each having two basal orange nectar glands and three staminodia. The anthers are tetrathecal.

*Pistil.*—The single pistil with a slender style and small stigmatic surface has one carpel with one ovule. The ovary is superior.

*Pedicel.*—Commonly approximately 7 mm in length and approximately 1.8 mm in diameter. The coloration is near yellow-green (RHS 145C).

*Number of flowers on inflorescence.*—There are approximately 90–180 flowers per inflorescence. In contrast, 'Merensky 2' has approximately 110–170 flowers per inflorescence.

*Fragrance.*—Absent.

*Bloom.*—Bloom period at Westfalia Estate Waterval section varies with temperatures. However the 'Merensky 1' variety has been found to bloom from 1$^{st}$ August through 10$^{th}$ October. In contrast, the 'Merensky 2' variety has been found to bloom from July 3$^{rd}$ through September 25$^{th}$.

Fruit:

*Length.*—11.2 cm.

*Width.*—7.0 cm.

*Ratio length/width.*—1.6.

*Shape.*—Obovate.

*Color of skin (when ripe).*—Light green (RHS 144A). In contrast, 'Merensky 2', very dark green (RHS 137A).

*Texture of skin.*—Rough, lenticels bumpy. In contrast, 'Merensky 2' very smooth.

*Presence of longitudinal ridges.*—Absent. In contrast, 'Merensky 2', one strong, long longitudinal ridge.

*Thickness of skin.*—Medium to thick when compared to other avocado varieties. In contrast, 'Merensky 2' is very thin and membranous. Also, by contrast, Bacon avocado skin is very thin and smooth.

*Adherence of skin to flesh.*—Weak. In contrast, 'Merensky 2' strong.

*Main color of flesh.*—Light yellow (RHS 154D).

*Color of intensely colored area of flesh next to skin.*—Yellow green (RHS 144A).

*Width of intensely colored area next to skin.*—3.0 mm.

*Conspicuousness of fibers in flesh.*—Conspicuous.

Seed:

*Length.*—5.1 cm. In contrast 'Merensky 2', 4.8 cm.

*Width.*—4.5 cm. In contrast 'Merensky 2', 4.2 cm.

*Shape.*—In longitudinal section — base flattened, apex rounded. In contrast, 'Merensky 2', ovate.

*Color of seed coat (fresh).*—Orange brown (RHS 165A).

Time of harvesting: March (in South Africa).

Resistance to pests: Strong resistance to *Phytophthora cinnamomi.*

Tolerance to salinity: Has shown higher salinity tolerance (significantly lower concentrations of chloride and sodium in leaves of the 'Hass' scion grafted onto 'Merensky 1') in a field trial than presently used avocado rootstocks.

Market use: The fruit of the present variety is not in condition for market use, but rather the variety is used as a rootstock onto which commercial varieties, such as 'Hass' are grafted.

We claim:

1. A new and distinct variety of *Persea americana* plant as illustrated and described.

* * * * *